US006451059B1

(12) United States Patent
Janas et al.

(10) Patent No.: US 6,451,059 B1
(45) Date of Patent: Sep. 17, 2002

(54) VISCOUS SUSPENSION SPINNING PROCESS FOR PRODUCING RESORBABLE CERAMIC FIBERS AND SCAFFOLDS

(75) Inventors: Victor F. Janas, Monroe Township; Kevor S. TenHuisen, Neshanic Station, both of NJ (US)

(73) Assignee: Ethicon, Inc., Somerville, NJ (US)

( * ) Notice: Subject to any disclaimer, the term of this patent is extended or adjusted under 35 U.S.C. 154(b) by 0 days.

(21) Appl. No.: 09/439,656

(22) Filed: Nov. 12, 1999

(51) Int. Cl.[7] .............................. A61F 2/28; A61F 2/02; B05D 3/00
(52) U.S. Cl. ................................ 623/23.51; 623/23.56; 623/23.75; 623/23.76; 427/2.27
(58) Field of Search .......................... 623/23.56, 23.51, 623/23.75, 23.76; 428/224; 427/2.27

(56) References Cited

U.S. PATENT DOCUMENTS

| | | | |
|---|---|---|---|
| 4,104,445 A | 8/1978 | Dobo | 428/567 |
| 4,118,225 A | 10/1978 | Dobo | 75/207 |
| 4,175,153 A | 11/1979 | Dobo et al. | 428/398 |
| 4,242,405 A | 12/1980 | Bockno | 426/224 |
| 4,245,000 A | 1/1981 | Bockno | 428/224 |
| 4,268,278 A | 5/1981 | Dobo et al. | 55/16 |
| 4,388,260 A | 6/1983 | Bockno | 264/168 |
| 4,405,549 A | 9/1983 | Turbak et al. | 264/188 |
| 4,613,577 A | 9/1986 | Tagai et al. | 501/35 |
| 4,655,777 A | 4/1987 | Dunn et al. | 623/16 |
| 4,735,857 A | 4/1988 | Tagai et al. | 428/388 |
| 4,810,449 A | 3/1989 | Reinehr et al. | 264/182 |
| 4,820,573 A | 4/1989 | Tagai et al. | 428/228 |
| 4,863,974 A | * 9/1989 | Mallouk et al. | 521/85 |
| 5,013,323 A | 5/1991 | Kobayashi et al. | 623/16 |
| 5,100,864 A | 3/1992 | Hsu | 505/1 |
| 5,413,858 A | 5/1995 | Hajikano et al. | 428/364 |
| 5,451,359 A | 9/1995 | Yahata et al. | 264/203 |
| 5,455,114 A | 10/1995 | Ohmory et al. | 428/364 |
| 5,468,544 A | 11/1995 | Marcolongo et al. | 428/224 |
| 5,615,466 A | 4/1997 | Safari et al. | 29/25.35 |
| 5,645,934 A | 7/1997 | Marcolongo et al. | 428/357 |
| 5,721,049 A | 2/1998 | Marcolongo et al. | 428/370 |
| 5,770,417 A | * 6/1998 | Vacanti et al. | 435/180 |
| 5,939,323 A | * 8/1999 | Valentini et al. | 435/395 |
| 6,136,029 A | * 10/2000 | Johnson et al. | 623/16.11 |

OTHER PUBLICATIONS

"Wet Spinning of a Single Layered Perovskite Y–Ba–Cu–O Superconductor" Tomoko Goto and Masanori Tsujihara; Journal of Materials Science Letters 7 (1988) p. 283.
"Fabrication of Continuous Ceramic Fiber by the Viscous Suspension Spinning Process" Richard B. Cass; Ceramic Bulletin, vol. 70, No. 3, 1991 pp 424–429.
"Developing Innovative Ceramic Fibers" Jonathan D. French and Richard B. Cass; The American Ceramic Society Bulletin; May 1998 pp 61–65.

* cited by examiner

*Primary Examiner*—David H. Willse
*Assistant Examiner*—Alvin Stewart

(57) ABSTRACT

The present invention provides a hard tissue scaffold comprising a resorbable ceramic. The scaffold is formed by first creating unfired (green) bioresorbable ceramic fibers via the viscous suspension spinning process (VSSP). Then, using common textile techniques, a structure in which the size and distribution of interconnected pores are controlled, is created. Heat treating the structure to remove the organic phase and sintering the ceramic yields a hard tissue scaffold.

24 Claims, 1 Drawing Sheet

1 mm 1 mm

10 μm

VISCOUS SUSPENSION SPINNING PROCESS FOR PRODUCING RESORBABLE CERAMIC FIBERS AND SCAFFOLDS

FIELD OF THE INVENTION

The present invention relates to resorbable ceramic fibers and scaffolds for use in biological application, and their method of production. Specifically, this invention relates to novel fibers and scaffolds, formed via a wet spinning technique, and useful as biological replacements for hard tissue.

BACKGROUND OF THE INVENTION

Bone grafts formed of porous calcium phosphates (CaP) show potential as a scaffolding for the growth of new bone in applications such as spinal fusion, long bone fractures, non-union fractures, bone defects, and hip revisions. In present devices, the porosity is either randomly distributed, or the manufacturing techniques have limited ability to control pore size. Control of pore distribution and size may be advantageous in optimizing bone growth into the graft.

The present invention relates to novel bone implants and their use in bone repair and reconstruction. More particularly, it relates to resorbable ceramic fibers and scaffolds, formed via a wet spinning technique, and useful as biological replacements for hard tissue. Bone grafts are used in the repair of significant fractures, the treatment of skeletal tumors, spinal fusion, and the reconstruction of failed total arthroplasties. Autogenous bone, or autograft, is bone harvested from another location in the patient, and used as the graft. Autograft performs very well in the applications cited above. The disadvantages of autograft include the limited supply of excess bone in the patient, as well as the inherent risks of morbidity and recovery pain taken by performing a second surgery. Allograft, bone taken from another human, has the advantage of being in larger supply than autograft bone. However, the greater immunogenic response of allograft, and risk of viral contamination or risk of transmission of live virus to the recipient, have led to the decline in use of allograft bone as a bone graft material. Xenograft, or bone grafts taken from another species, often elicits acute antigenic response. In the vast majority of cases, xenograft fails in its role as a graft material.

Synthetic bone graft materials have been described in Bone Graft and Bone Graft Substitutes: A Review of Current Technology and Applications; Damien and Parsons; *J. Applied Biomaterals*, Vol. 2, 1991, pages 187–208, which is incorporated herein by reference. The ideal graft should be able to support a load equivalent to the bone that is being replaced, so that the newly formed bone can remodel to the same quality and dimensions of the original bone that is being replaced. Ideal graft is also osteoactive, enhancing the formation of new bone. This is achieved both by the chemical nature of the material, as well as the structure, or architecture of the graft. Structurally, the graft needs to be porous to allow for ingrowth of the new bone. Though no optimal pore size has been established, the size of the pores required for good bone growth is between 100 and 500 microns. The ability to tailor the pore size and distribution is also viewed as a method of enhancing bone growth. Load support can be achieved by having the supporting phase of the graft three-dimensionally connected.

The materials in bone graft substitutes include, but are not limited to, plaster of Paris (calcium sulfate, $CaSO_4 \cdot 1/2H_2O$) tricalcium phosphate ($Ca_3(PO_4)_2$), hydroxyapatite ($Ca_{10}(PO_4)_6(OH)_2$), calcium phosphate cements, calcium aluminates, the family of Bioglass® (composed of $SiO_2$, $Na_2O$, $CaO$, and $P_2O_5$), apatite-wollastinite glass-ceramics (AWGC), polymers such as polymethylmethacrylate (PMMA) or polyhydroxyethylmethacrylate (PHEMA), and blends of the above. They may be in the form of loose particles, particles bound in polymer or other carrier material (a paste), ceramic precursors that react when blended together (calcium phosphate cements), porous solids, or loose fiber constructs (such as felts), or textile processed fibers (weaves, braids, or knits).

The disadvantages of using loose particles as a bone graft include the difficulty of handling them, the tendency of the particles to settle (or pack tightly) into the defect, the inability of loose particles to support load, and particle migration away from the defect site in bodily fluids. Particle settling results in two problems. First, when the particles pack together, the pore size is reduced in the graft to less than 100 $\mu$m. This pore size does not allow the migration and ingrowth of cells into the graft. Particle settling also results in an inability to control the pore size and distribution in these systems. The size and distribution of pores in these types of grafts are determined by the size of the particles and how they pack together. Since settling is not controllable, there is no ability to use graft architecture to control new bone growth into the graft. Particle migration from the site results in possible tissue irritation and undesired tissue response in regions were the particles eventually settle.

Particle settling and migration problems have been mitigated to some extent by the use of synthetic or natural matrix materials, including polymers such as PMMA, polysulfone (PS), or polyethylene (PE), which are not resorbable, and ceramics, such as plaster of Paris or calcium phosphate cements. Particles have also been enclosed in tubes of resorbable polymers, such as collagen or polyglycolide. The size and distribution of pores in these types of grafts are also not controllable. The distribution is determined by the size of the particles, how they pack together, and the relative proportions of the matrix and particle phases. As with loose particles, there is limited ability to use graft architecture to control new bone growth into the graft.

For bone grafts in the form of cements, there is also a limited ability to control the pore size and distribution. Pore creating agents may be put into the cement prior to its formation. However, the size and distribution of pores are determined by the size, form, and concentration of the agent, resulting in the inability to use graft architecture to control new bone growth into the graft. This inability to control pore size and distribution also results in limits in load support capability. A random distribution of pores results in a random distribution of defects in the structure. So, although the load-supporting phase of the graft is three-dimensionally connected, these types of grafts have shown low load support capability. Control of the pore size and distribution in porous solid bone grafts is also limited. Porous solid bone grafts have been formed using the replamine process on naturally occurring coral. Here, the pore size and distribution is limited to that of the species of coral used. Defect location is also uncontrollable, lowering the load support capability of the graft in a fashion similar to that discussed above for cements. Pore creating agents may also be put into a ceramic prior to its formation. But, as is the case with cements, the size and distribution of pores are determined by the size, form, and concentration of the agent.

Bone grafts in the form of textile architectures, such as weaves, braids, or knits, have advantages over the other forms of bone grafts. Textile technology may by used to precisely place the fibers in a desired location in space, allowing for a large degree of control in the size and distribution of pores in the bone graft structure. However, since there is no interconnection of fiber in three dimensions, load support capabilities of grafts of this type are limited.

There are a number of woven structured formed with fibers composed of the materials found in bone graft substitutes cited in the prior art. Tagai et al., in U.S. Pat. Nos. 4,820,573, 4,735,857, and 4,613,577, disclose a glass fiber provided for the filling of a defect or hollow portion of a bone. In this case, the calcium phosphate glass fiber may be in the form of short fibers, continuous fiber, or woven continuous fibers. In this prior work, the load support capability of the graft is limited since there is no interconnection of fiber in three dimensions.

To increase the strength of the fibrous implants, bioresorbable fibrous constructs have been filled with polymers to form composite structures. Many of these have been cited in the prior art. U.S. Pat. No. 5,013,323, to Kobayashi et al., discloses an implant material for replacing hard tissue composed of calcium phosphate glass fibers in an organic polymer, where some of the glass fiber on the composite surface is exposed to the living tissue to promote bonding of the device to the tissue.

In U.S. Pat. Nos. 5,721,049, 5,645,934, and 5,468,544 (all to Marcolongo et al.), disclose composite materials formed from bioactive glass or ceramic fibers. The preferred embodiments are braids or meshes of bioactive glass or ceramic fiber interwoven with structural, non-bioactive fibers impregnated with a polymer to form a composite of suitable biocompatibility and structural integrity. The braid or mesh is designed so that the bioactive fibers are concentrated on the surface of the implant.

A method of producing biodegradable prostheses comprising a composite of resorbable fibers reinforcing a biodegradable matrix is disclosed in U.S. Pat. Nos. 4,655,777 (Dunn & Kasper), and 4,604,097 (Graves & Kumar). Both patents will be discussed in greater detail below. The fibers include ceramics, such as tricalcium phosphate, and a biodegradable glass. In this case, the fiber/polymer composite is made in the laminated form, and not as a woven structure.

The limitation of the composite approach is that by filling in the space between the fiber, the structures themselves are no longer porous. They are therefore unable to support the ingrowth of new bone. As discussed earlier, pore creating agents may also be put into the composite prior to its formation. However, as pointed out for earlier structures, the size and distribution of pores are determined by the size, form, and concentration of the agent.

The fibers produced in the patents cited above have a wide variety of compositions, and were formed by various techniques. In most cases, they are composed of mixtures of silicon dioxide ($SiO_2$), aluminum oxide ($Al_2O_3$), calcium oxide (CaO), sodium oxide ($Na_2O$), potassium oxide ($K_2O$), lithium oxide ($Li_2O$), magnesium oxide (MgO), zinc oxide (ZnO), strontium oxide (SrO), iron oxide ($Fe_2O_3$), titanium oxide ($TiO_2$), zirconium oxide ($ZrO_2$), calcium fluoride ($CaF_2$), and phosphorous pentoxide ($P_2O_5$). These compositions are melt spun at temperatures between 800 and 1700° C. A discussion of the range of spinnable, degradable glass compositions, and how they are processed, is discussed in U.S. Pat. No. 4,604,097 (Graves & Kumar).

The bioresorbable ceramic fibers for use as the reinforcement phase in a laminated fiber/polymer composite discussed in U.S. Pat. No. 4,655,777 (Dunn & Kasper) were produced via a wet spinning technique known as the viscous suspension spinning process (VSSP). VSSP will be discussed in detail later. As mentioned earlier, these fibers are used in laminated form in fiber/polymer composites, and not as a woven structure. Wet spinning has been utilized to create heat resistant fibers (U.S. Pat. No. 4,976,884, to Delvaux and Lesmerises) by adding ceramic materials to the organic binder prior to fiber spinning. The wet spinning technique has also produced carbon fiber (U.S. Pat. No. 4,869,856 to Takahashi and Yagi) by heat treating the spun acrylonitrile fibers in a reducing atmosphere. Metal fibers (U.S. Pat. Nos. 4,118,225, and 4,104,445, to Dobo) and superconducting ceramic fibers (U.S. Pat. No. 5,100,049 to Hsu, and Goto and Tsujihara, in *J. Mater. Sci. Letters*, 7[3] 238, 1988) have been formed by adding metal or ceramic powders to the binder, spinning the fibers, and heat treating the fibers in the proper environment to eliminate the binder and sinter the metal or ceramic powders. Hollow metal and ceramic fibers have also been produced by adding metal or ceramic powders to the binder as discussed above, spinning the fibers through a hollow tube spinerette, and heat treating the spun fibers as discussed above. Ceramic powders have also been added to rayon viscous precursor solution, and green (unsintered) fibers have been spun in the viscous suspension spinning process (VSSP).

The green VSSP fibers may be heat treated in the proper environment to eliminate the binder and sinter the ceramic, yielding a ceramic fiber. Many ceramic fibers, such as titanium dioxide, silicon carbide, zirconium oxide (French and Cass, in *Ceramic Bulletin*, 77[5] 61, 1998, and Cass, in *Ceramic Bulletin*, 70[3] 424, 1991), and lead zirconate titanate (McNulty et al. in *J. Amer. Ceram. Soc.*, 78[11] 2913, 1995) have been created this way.

As mentioned above, bioresorbable ceramic fibers for use as the reinforcement phase in a laminated fiber/polymer composite were produced via the VSSP process. In U.S. Pat. No. 4,655,777 (Dunn & Kasper), the forming of β-tricalcium phosphate (β-$Ca_3(PO_4)_2$) and calcium aluminate ($CaAl_2O_4$) fibers is disclosed. The fibers were produced by extruding a mixture of ceramic powder, binder, and solvent into a bath containing a non-solvent for the binder. During extrusion into the non-solvent bath, the mixture coagulates to form a filament. These filaments are subsequently drawn down into fibers over a series of godets, rinsed to remove residual solvent, dried, and heat treated in an inert atmosphere to sinter the ceramic. As mentioned earlier, these fibers are used in laminated form in fiber/polymer composites, and not as a woven structure.

In summary, the prior art presents a number of methods for forming synthetic bone grafts. In all cases, the forming techniques lack the ability to tailor the pore size and distribution in the graft, and/or the ability to have the supporting phase of the graft three-dimensionally interconnected. Tailored pore size is viewed as a method of enhancing bone growth, while improved load support is achieved by a three-dimensionally connected supporting phase.

It is therefor an object of the present invention to provide a bone graft in which the pore size and distribution is tailored to enhance bone growth, and improved load support is achieved by a interconnected three-dimensional support phase.

Another object of this invention is to create structures to use as scaffolds for the in vitro or in vivo growth of human or animal tissue, such as bone or cartilage. These scaffolds can be used as implant materials for the replacement of defects or hollow portions of hard tissue resulting from external injury or surgical removal of hard tissue tumors. Their composition can be tailored such as to be resorbed by the body at a rate equivalent to the rate at which natural hard tissue grows into the above mentioned defects or hollow portions of hard tissue.

A still further object of this invention is the formation of laminated bioresorbable structures where each layer has controlled pore size and distribution. This type of structure has another degree of control for optimizing bone growth into the resorbable ceramic structure if the structure is used as bone graft.

SUMMARY OF THE INVENTION

We have discovered a process for making unified three-dimensional bioresorbable ceramic structures for use as bone replacement materials in which pore size and distribution are controlled. The structure is formed by first creating unfired (green) bioresorbable ceramic fibers via the viscous suspension spinning process (VSSP). Then, using common textile techniques, such as weaving, braiding, or knitting, a structure in which the size and distribution of interconnected pores are controlled, is created. Heat treating the structure to remove the organic phase and sintering the ceramic yields a hard tissue scaffold. The advantage of this work over biocompatible inorganic structures disclosed in the past is the ability to both control pore size and distribution for optimized bone ingrowth, as well as for a unified three-dimensional ceramic structure with load support capability.

DETAILED DESCRIPTION OF THE INVENTION

Figure 1:
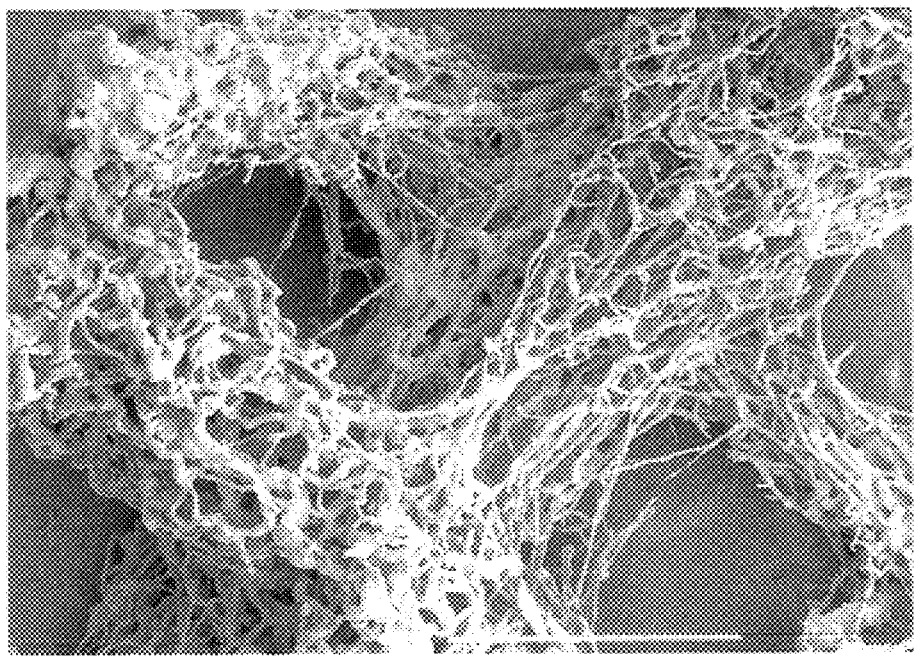
FIG. 1 is a photomicrograph at low magnification of a woven bioceramic structure.

We have discovered a process for making novel hard tissue scaffold using the viscous suspension spinning process (VSSP) to create unfired (green) bioresorbable ceramic fibers. Textile techniques are used to create a structure in which the size and distribution of interconnected pores are controlled. Heat treating the structure to remove the organic phase, and sintering the ceramic, yields a resorbable hard tissue scaffold.

Formation of the scaffold starts with readily available bioresorbable inorganic powders with tailored resorption characteristics, such as hydroxyapatite, tricalcium phosphate, tetracalcium phosphate, or other amorphous or crystalline phosphate, or multi-phasic blends of resorbable glasses and/or sinterable ceramics. For polycrystalline ceramics, the powder used in the process is very fine (<10 $\mu$m granule size). This fine size is required for the firing step in the process. Granules of significantly larger size will not merge together to form fully connected fibers in the subsequent processing steps discussed below.

The powder is combined with compatible polymers or prepolymers, and then wet spun to form powder/polymer fibers. Compatible polymers are polymers that can be solution spun from a solution that is non-reactive with the powders described above and does not leave an undesirable residue on firing. Suitable compatible polymers include but are not limited to polyvinyl alcohol, polyethylene glycols, cellulose-based polymers, and natural polymers such as gelatin and guar gums. One such compatible polymer is Viscose. Viscose is prepared by taking sheets of cellulose obtained from wood pulp or cotton linters, shredding the sheets into crumbs, and mixing with solvents, such as water, until a solution is formed. In this work, the biocompatible powders were mixed into a cellulose/water solution containing sodium hydroxide in a high shear mixer.

Wet spinning is well documented for forming a number of organic, metal, and ceramics fibers. Most of the discussion below, although unrelated to the current invention, serves as a means of clarifying the types of fibers formed by the wet spinning process used in this invention.

Wet spinning has been used to make a number of organic fibers, including those composed selected from the groups consisting of cellulosics (rayon etc.), polyvinyl alcohols (U.S. Pat. No. 5,455,114, to Ohmory et al. incorporated herein by reference) polyesters (U.S. Pat. No. 5,451,359, to Yahata and Tsukamoto incorporated herein by reference) and combination thereof. In all cases, the polymer to be made into a fiber is dissolved in a solvent to create a spinning dope. The dope is passed through a multi-hole spinneret into a solidifying bath. The bath solidifies the dope into gel (no change in dope composition) or coagulate (change in dope composition) fibers. The same solidifying bath may also be used to remove the dope solvent in the fibers by extraction. The fibers are drawn down to a smaller diameter either in or out of the solidifying bath.

Residual solvent is removed in a series of washing and drying steps. The resulting fiber may or may not be further drawn down to a smaller diameter, if desired. Rayon fibers have been prepared by spinning a viscous solution (see, for example, U.S. Pat. No. 4,405,549, to Turbak and Hartmann, U.S. Pat. Nos. 4,388,260, 4,245,000, and 4,242,405, to Bockno).

In this work, inorganic/polymer fibers were created by passing the mixture of biocompatible powders in cellulose/water solution described above through a multi-hole spinneret into a solidifying bath. The bath solidified the mixture. The fibers were drawn down to a smaller diameter in the bath. Residual solvent was removed in a series of washing and drying steps.

At this point, the fibers, containing both inorganic materials and their organic binders, are formed into three-dimensional structures via conventional textile techniques such as weaving, braiding, and knitting. Textile technology is used to precisely place the fibers in a desired location in space, allowing for a large degree of control in the size and distribution of pores in the structures disclosed in this work.

As mentioned earlier, in biocompatible inorganic fibrous structures disclosed in the past, the fibers were not unified in a three-dimensional structure. Therefor, load support capabilities of these structures is limited. In this work, the structures are formed into three-dimensional structures in the green (unfired) state. Firing is accomplished by exposing the structures to temperatures sufficient to cause the removal of the organic binders by sublimation or oxidation, and the inorganics to bond in a process known in the ceramics field as sintering. When fired, the fibers will cross-sinter with one another, resulting in a three-dimensionally connected ceramic tissue scaffold structure in which pore size and distribution are controlled.

With this invention, there is opportunity for the formation of laminated structures, and a countless number of three-dimensional structures. The individual plies can be formed via textile operations such as weaving, braiding and knitting. Mixed fabric types can be incorporated into the structure for further control of pore size and distribution. Though no optimal pore size and distribution has been established, the size of the pores required for good bone growth is between 100 and 500 microns. The ability to tailor the pore size and distribution is also viewed as a method of enhancing bone growth.

The structures created by this invention may be used as scaffolds for the in vitro or in vivo growth of human or animal tissue, such as bone or cartilage. These scaffolds can be used as a novel implant material for the replacement of defects or hollow portions of hard tissue resulting from external injury or surgical removal of hard tissue tumors. Their composition can be tailored such as to be resorbed by the body at a rate equivalent to the rate at which natural hard tissue grows into the above mentioned defects or hollow portions of hard tissue.

In addition, the three-dimensional structure may be filled with resorbable synthetic polymers or biopolymers or ceramic materials that may or may not contain materials that promote bone growth through the device. These include autograft, allograft, or xenograft bone, bone marrow, demineralized bone (DBM), natural or synthetic bone morphogenic proteins (BMP's i.e. BMP 1 through 7), bone morphogenic-like proteins (i.e. growth and differentiation factor 5 (GFD-5) also known as cartilage-derived morphogenic factor 1, GFD-7 and GFD-8) epidermal growth factor (EGF), fibroblast growth factor (FGF i.e. FGF 1 through 9), platelet derived growth factor (PDGF), insulin like growth factor (i.e. IGF-I and IGF-II and optionally IGF binding proteins), transforming growth factors (TGF-$\beta$ i.e. TGF-$\beta$I through III), vascular endothelial growth factor (VEGF) or other osteoinductive or osteoconductive materials known in the art. Biopolymers could also be used as conductive or chemotactic materials, or as delivery vehicles for growth factors. Examples could be recombinant or animal derived collagen or elastin. Bioactive coatings or surface treatments could also be attached to the surface of the device. For example, bioactive peptide sequences (RGD's) could be attached to facilitate protein adsorption and subsequent cell tissue attachment. Antibiotics could also be coated on the surface of the device or delivered by a material within the device.

The polymeric materials filling the device could exist in a number of phases including solids, foams, or liquids. The structure could be filled polymer to some specified degree to improve the mechanical toughness of the device. Foamed polymeric materials could be lyophilized within the structure providing a scaffold within a scaffold. The porous polymeric foam would provide an osteoconductive medium for bone growth into the device. The porous foam could also serve as a delivery medium for growth factors, peptides, and other bioactive materials.

The three-dimensional structure could also be filled with photocurable polymeric materials and cured in place with UV light source. It could also be filled with ceramic cements, monolithic ceramic materials or particles that are osteoconductive or inductive. The structure could also be post-processed with a ceramic or polymeric coating that is osteoconductive or inductive. The second ceramic material would act as a coating that would be different from the materials used for the main body of the scaffold.

The three-dimensional structure may also serve as a scaffold for the engineering of bone tissue to facilitate bone healing. The structure may have an internal porous structure that would be conducive to the growth of cells. As outlined in previous patents (Vacanti, U.S. Pat. No. 5,770,417), tissue can be harvested from a patient and the tissue can be sterile processed to provide a specific cell type (i.e., osteoblast, mesenchymal stem cell (Caplan, U.S. Pat. No. 5,486,359), etc.). The cells could contain inserted DNA encoding a protein that could stimulate the attachment, proliferation or differentiation of bone tissue. The three-dimensional structure would be placed in cell culture and the cells seeded onto or into the structure. The structure would be maintained in a sterile environment and then implanted into the donor patient once the cells have invaded the microstructure of the scaffold. The in vitro seeding of cells could provide for a more rapid healing process. Additionally, radio-opaque markers may be added to the scaffold to allow imaging after implantation. Without intending to limit it in any manner, the present invention will be more fully described by the following examples.

EXAMPLE 1

Particles of ceramic tricalcium phosphate, $Ca_3(PO_4)_2$, with a BET surface area of 1.708 $m^2$/gm, were milled in water containing a sodium silicate surfactant to create a dispersion. The dispersion was added to a viscose, which had previously been made by dissolving cellulose in a sodium hydroxide (NaOH) solution. The ratio of ceramic particles to cellulose in the mix was 70 to 30 by weight.

The mix was pumped through a 100-hole, 90-micron spinneret into a solution of sulfuric acid ($H_2SO_4$) which, after subsequent washes in mild acid solutions and water, yielded a tow of cellulose fibers highly filled with ceramic phosphate & sulfate particles.

Approximately 1 gram of yarn was placed on platinum foil, which in turn was put onto an aluminum setter plate, and placed in a high temperature furnace. The following heat treatment schedule was followed (under an air atmosphere): ramp from room temperature to 150° C. in 2 hours, hold 150° C. for 2 hours, ramp from 150° C. to 550° C. in 13 hours, hold 550° C. for 2 hours to allow for removal of the cellulose, ramp from 550° C. to 1050° C. in 2 hours, hold 1050° C. for 2 hours to allow for sintering of the ceramic particles, ramp from 1050° C. to room temperature in 4 hours.

The resulting ceramic fibers were examined under X-ray Diffraction and spectrochemical analysis to determine their chemical composition and crystalline structure. The analyses showed the fibers to be a multi-phasic blend of calcium sulfates, sodium sulfates, calcium phosphates, and sodium phosphates. By weight, the fibers were 52% $SO_4$, 37% CaO, 4.5% $P_2O_5$, 3.6% $Na_2O$, and approximately 3% of trace compounds such as $SiO_2$ and ZnO.

EXAMPLE 2

Tows of cellulose fibers highly filled with tricalcium phosphate particles, made as described in Example 1, were woven into simple flat panels by hand. The weave pattern used was a simple "one over, one under" plain weave. Several of the weaves were placed on platinum foil, which in turn was put onto an aluminum setter plate, and placed in a high temperature furnace. The following heat treatment schedule was followed (under an air atmosphere): ramp from room temperature to 550° C. in 3 hours, hold 550° C. for 2 hours to allow for removal of the cellulose, ramp from 550° C. to 1050° C. in 2 hours, hold 1050° C. for 2 hours to allow for sintering of the calcium phosphate particles, ramp from 1050° C. to 550° C. in 4 hours.

Figure 2:
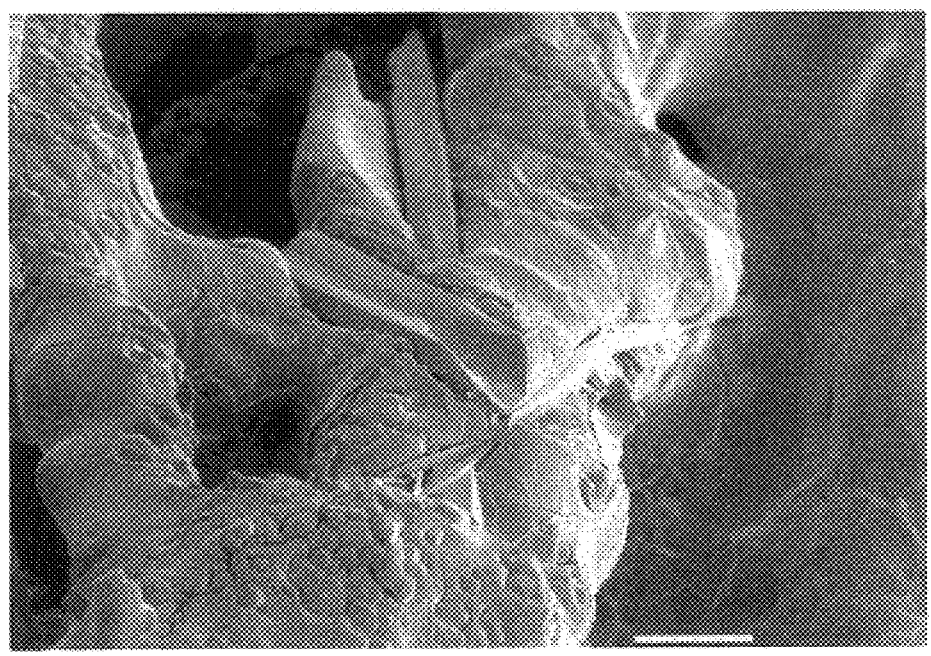
FIG. 2 is a photomicrograph of a section of FIG. 1 but taken at a higher magnification.

The resulting ceramic scaffold was examined under Scanning Electron Microscopy (SEM). The scaffold maintained the woven architecture of the unfired weave. FIG. 1 is an SEM photograph of the woven structure. The figure shows the large pores (100–1000 μm) which have been associated with good tissue growth into a scaffold. FIG. 2 shows the same scaffold at a higher magnification. In this SEM, individual ceramic fibers are clearly visible, as are the fine pores (<100 μm) between the fibers. The fine pore structure could serve as a reservoir for natural and synthetic agents that promote bone growth into the scaffold.

We claim:

1. A process for making a biocompatible ceramic implant device, comprising the following steps:
   a) solution spinning a biocompatible calcium phosphate powder within an organic phase comprising a biocompatible organic polymer to create an unfired bioresorbable ceramic fiber;
   b) processing the unfired bioresorbable ceramic fiber to form a three-dimensional structure in which size and distribution of interconnected pores are controlled; and
   c) heat treating the structure to remove the organic phase and sinter the bioresorbable ceramic fiber, to yield biocompatible, resorbable hard tissue scaffolds comprising ceramic fibers cross-sintered with one another.

2. The process of claim 1 wherein the calcium phosphate is selected from the group consisting of hydroxyapatite, tricalcium phosphate, tetracalcium phosphate, and multi-phasic blends of resorbable glasses and ceramics.

3. The process of claim 1 wherein the biocompatible polymer is selected from the group consisting of synthetics, cellulosics, polyvinyl alcohols, polyesters, and combination thereof.

4. The process of claim 1 wherein the three-dimensional structure is formed by a textile process selected from the group consisting of weaving, knitting, and braiding.

5. The process of claim 1 wherein the ceramic surfaces of the scaffold are treated to promote bone growth through the scaffold.

6. The process of claim 1 wherein the interconnected pores of the scaffold are coated with materials which promote bone growth through the scaffold.

7. The process of claim 1 wherein the interconnected pores of the scaffold are filled with natural or synthetic materials which promote bone growth through the scaffold.

8. The process of claim 1 wherein the interconnected pores of the scaffold are filled with resorbable polymers which improve the mechanical properties of the scaffold.

9. The process of claim 1 wherein the interconnected pores of the scaffold are filled with resorbable polymers containing natural or synthetic materials which promote bone growth through the scaffold.

10. The process of claim 1 wherein the scaffold is filled with a porous open cell foam made from an absorbable polymer.

11. The process of claim 1 wherein cells are grown on the scaffold in vitro.

12. The scaffold of claim 1 wherein the scaffold is seeded with cells.

13. The process of claim 1 wherein the scaffold is seeded with cells.

14. A process for making a biocompatible bioresorbable ceramic implant device, formed by the following steps:
   a) using a viscous suspension spinning process to spin a solution containing a biocompatible calcium phosphate powder dispersed in an organic phase containing a suitable organic polymer to create an unfired bioresorbable ceramic fiber;
   b) using common textile techniques to form the bioresorbable unfired ceramic fiber into a three-dimensional structure in which size and distribution of interconnected pores are controlled; and
   c) heat treating the structure to remove the organic phase and sinter the bioresorbable ceramic fiber, to yield a biocompatible, resorbable hard tissue scaffold comprising ceramic fibers cross-sintered with one another.

15. The process of claim 14 wherein the calcium phosphate is selected from the group consisting of hydroxyapatite, tricalcium phosphate, tetracalcium phosphate, and multi-phasic blends of resorbable glasses and ceramics.

16. The process of claim 14 wherein the biocompatible polymer is selected from the group consisting of synthetics, cellulosics, polyvinyl alcohols, polyesters, and combination thereof.

17. The process of claim 14 wherein the three-dimensional structure is formed by a textile process selected from the group consisting of weaving, knitting, and braiding.

18. The process of claim 14 wherein the ceramic surfaces of the scaffold are treated to promote bone growth through the scaffold.

19. The process of claim 14 wherein the interconnected pores of the scaffold are coated with materials which promote bone growth through the scaffold.

20. The process of claim 14 wherein the interconnected pores of the scaffold are filled with natural or synthetic materials which promote bone growth through the scaffold.

21. The process of claim 14 wherein the interconnected pores of the scaffold are filled with resorbable polymers which improve the mechanical properties of the scaffold.

22. The process of claim 14 wherein the interconnected pores of the scaffold are filled with resorbable polymers containing natural or synthetic materials which promote bone growth through the scaffold.

23. The process of claim 14 wherein the scaffold is filled with a porous open cell foam made from an absorbable polymer.

24. The process of claim 14 wherein cells are grown on the scaffold in vitro.

* * * * *